United States Patent
Deluca et al.

(10) Patent No.: US 6,508,104 B1
(45) Date of Patent: Jan. 21, 2003

(54) METHOD FOR ADDITIVE ADHESION FORCE PARTICLE ANALYSIS AND APPARATUS THEREOF

(75) Inventors: Allen F. Deluca, Webster, NY (US); Timothy L. Lincoln, Rochester, NY (US); Hon H. Le, Webster, NY (US); Christine L. Demay, Ontario, NY (US); Eric Murray, Webster, NY (US); David A. Allen, Webster, NY (US); Leela Ganguly, Webster, NY (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/680,066

(22) Filed: Oct. 5, 2000

(51) Int. Cl.$^7$ .............................................. G01N 35/04
(52) U.S. Cl. .................... 73/53.01; 73/61.41; 73/61.71; 73/61.72; 73/61.75
(58) Field of Search ............................ 73/53.01, 61.41, 73/61.71, 61.72, 61.75, 64.48, 150 A

(56) References Cited

U.S. PATENT DOCUMENTS

| | | | |
|---|---|---|---|
| 4,323,119 A | * 4/1982 | Bodine | .................... 166/177.1 |
| 4,537,599 A | * 8/1985 | Greenwald, Sr. | ............. 44/550 |
| 4,639,356 A | 1/1987 | O'Toole et al. | |
| 4,741,841 A | 5/1988 | Borre et al. | |
| 4,774,958 A | * 10/1988 | Feinstein | .................... 424/9.52 |
| 4,849,318 A | * 7/1989 | Tsubota et al. | .............. 430/137 |
| 4,943,759 A | 7/1990 | Sakamoto et al. | |
| 5,178,836 A | * 1/1993 | Kitamori et al. | ............... 422/73 |
| 5,259,254 A | 11/1993 | Zhu et al. | |
| 5,376,182 A | * 12/1994 | Everett et al. | ............. 134/25.1 |
| 5,400,665 A | 3/1995 | Zhu et al. | |
| 5,476,745 A | * 12/1995 | Nakamura et al. | .......... 430/137 |
| 5,515,716 A | * 5/1996 | Poziomek et al. | .......... 73/61.41 |
| 5,840,026 A | 11/1998 | Uber, III et al. | |
| 6,045,913 A | * 4/2000 | Castle | ......................... 428/403 |
| 6,074,794 A | * 6/2000 | Fushimi et al. | ............. 430/109 |
| 6,270,837 B1 | * 8/2001 | Liu et al. | ..................... 427/180 |
| 6,284,282 B1 | * 9/2001 | Maa et al. | ................... 424/499 |
| 6,318,158 B1 | * 11/2001 | Breen et al. | ................ 73/64.56 |

FOREIGN PATENT DOCUMENTS

JP      1-152366     * 6/1989 ................. 435/7.1

* cited by examiner

Primary Examiner—Daniel S. Larkin
(74) Attorney, Agent, or Firm—Robert Thompson

(57) ABSTRACT

A method including: sonicating a liquid suspension of first particles; and analyzing the liquid phase for second particles. An apparatus including: a sonicator adapted to sonicate a liquid suspension of first particles; and a first analyzer adapted to analyze the sonicated liquid phase for second particles. The method and apparatus can be used to analyze the adhesion force relationships between the main or host first particles and guest or surface additive second particles.

27 Claims, 4 Drawing Sheets

METHOD FOR ADDITIVE ADHESION FORCE PARTICLE ANALYSIS AND APPARATUS THEREOF

BACKGROUND OF THE INVENTION

The present invention is generally directed to a method and apparatus for measuring the adhesive force of smaller surface additive particles to larger particles. More specifically the present invention is directed to a multi-horn ultrasonic agitator system which enables precise control of ultrasonic energy output from the horns and which system permits the analysis of, for example, liquid and solid phases, and small surface additive constituents(guest particles) residing on larger sized particulates(host particles). The present invention also provides automated robotic control and sample handling for efficient and automatic operation. The present invention provides methods and apparatuses for host and guest particle separation or host and guest particle extraction. The present invention provides an analytical tool to characterize the amount of guest surface additive(s) on and off the host or main particles, such as toners versus the amount of surface additive irrevocably impacted on the surface of the main particles. The resulting data can be readily correlated to host particle, guest particle, or subparticle performance and associative states or dispositions, such as toner and developer imaging performance. The present invention provides a system and method for removing additives from the surface of toner particles and other surface treated particles by way of controlled automated ultrasonic energy input. These and other embodiments of the present invention disclosed herein.

In a typical electrostatographic printing system, a light image or digital image of an original to be reproduced is recorded in the form of an electrostatic latent image upon a photosensitive member and the latent image is subsequently rendered visible by the application of electroscopic thermoplastic resin particles which are commonly referred to as toner. The visible toner image is then in a loose powdered form and can be easily disturbed or destroyed. The toner image is usually fixed or fused upon a support which may be the photosensitive member itself or another support sheet such as plain paper. Other related marking technologies are known, for example, liquid immersion development, and solid or liquid ink jet imaging technologies wherein a liquid, solid, molten, sublimed, and the like marking formulations are deposited onto an imaging member, imaging intermediate member, or image receiver and wherein the marking or imaging material is typically conveniently packaged for end-user or operator installation. Thus, it is readily apparent to one of ordinary skill in the art that embodiments of the present invention are readily adaptable to other marking formulations and other marking materials, and related consumable materials, such as, replenishers, liquid inks or developers, photoactive pigments and surface treated photoactive pigments, photoreceptors, fuser rolls constituents, backer rolls, fuser oils, cleaning formulations, papers or transparency stock, such as high quality or specialty receivers, "T" shirt transfer compositions and components, and the like materials. It is also readily apparent to one of ordinary skill in the art that embodiments of the present invention are readily adaptable to other analytical technological endeavors, for example, pharmaceutical dosage form formulation and analysis, agri-product formulation and analysis, particulate and fiber forensic analysis, and like applications.

In embodiments, the system and methods of present invention provide unexpected benefits and superior productivity performance levels to analysts or operators, for example, in facilitating unique or high volume sample analysis and result obtention, and in enabling sample of analysis of liquid suspended particulate materials and without the need for caustic or corrosive reagents to prepare dissolved analytes, for example hydrofluoric acid solutions for ion coupled plasma (ICP) analysis of inorganic and organo-metallic materials. These and other advantages of the present invention are illustrated herein.

PRIOR ART

In U.S. Pat. No. 4,741,841, issued, May 3, 1988, to Borre et al., there is disclosed a method and apparatus for particle separation where particulates which are less than and greater than a predetermined size and are entrained in a fluid are separated according to their respective sizes by passing the fluid and entrained particulates through a porous, cross-flow separator element while continuously vibrating the separator element to prevent buildup of particulates on the upstream side of the separator element.

In U.S. Pat. No. 5,400,665, issued Mar. 28, 1995, and U.S. Pat. No. 5,259,254, issued Nov. 9, 1993, both to Zhu, et al., there is disclosed an efficient sample introduction system and method of use, for accepting liquid sample solutions, nebulizing them to form nebulized sample solution droplets, desolvating and removing solvent therefrom, and introducing the resulting desolvated nebulized sample particles to sample analysis systems such as ICP. In the preferred embodiment, a flow of heated gas is caused to flow over the outer surface of a coiled essentially tubular shaped enclosed filter to remove solvent vapor which diffuses through the coiled essentially tubular shaped enclosed filter while a mixture of desolvated nebulized sample particles and solvent vapor is caused to flow therethrough. A modified embodiment utilizes a low temperature condenser in place of the heated gas flow. Nebulization of sample solutions is accomplished by use of high efficiency ultrasonic or direct injection micro nebulizer systems. Desolvation is performed in a desolvation chamber in which heating elements provide a temperature sufficient to vaporize solvent present. The sample introduction system provides improved sample solution nebulization, desolvation and solvent removal, as well as reduced sample loss and carry-over of sample from one analysis procedure to a subsequent analysis procedure, as compared to other systems no which perform a similar overall function. The sample introduction system also enhances transport of sample through the sample introduction system to a sample analysis system. The present invention is equally effective with sample solutions in which the sample solvent is either water, or an organic solvent.

Other references of interest include U.S. Pat. Nos. 4,639,356, which discloses the use of ultrasound for agitative mixing and atomization in preparing ceramic materials; U.S. Pat. No. 5,840,026 which discloses an electronic control means, including feedback control, for calculating flow rate and concentration of the fluid medium, such as an ultrasound imaging agent, based on characteristic data of a sample, such as a patient; and U.S. Pat. No. 4,943,759 which discloses a multiple-articulated robot feedback control apparatus. The aforementioned patent references are incorporated in their entirety by reference herein.

There remains a need for simple, efficient, safe, economical, and highly reliable and reproducible method and apparatus for the analysis of the relationship between host-guest particle combinations and the like industrial, environmental, or specialty formulations.

The system of the present invention is useful, for example, in electrophotographic imaging materials analysis, diagnostics, development, and the like applications, especially color and digital applications. As a specific example, the present invention can be used in the design and manufacture of superior flow and charge performing toner materials, such as silica surface treated resin based toners. As another example, the present invention can be used for tracking and elucidating trends in solid area density values (SAD) during xerographic print testing. Another area of application of the system, apparatus, and method of the present invention, includes for example, as a useful tool in the design, manufacture, diagnosis, or trouble shooting performance, of particle materials or particulate containing formulations, such as found in the imaging materials technology area, for dry or liquid xerography, ionography, magnetography, silver halide photography, and the like technology areas. Other areas of application of the system, apparatus, and method of the present invention, include for example, pharmaceutical dosage form analysis, including for example, timed release, delayed release, or controlled release formulations. Still other areas of application of the system, apparatus, and method of the present invention, include for example, secondary particulate emission analysis, that is measurement of materials on the surface of the primary emitted particles, such as sub-particles or liquid adsorbates including dust or oil, as found for example, on the surface of particulate emissions from for example, combustion or engine exhaust, smoke stacks, and the like sources of particulate emissions and the like effluents. Representative technology areas include for example: environmental testing and analysis; pesticide and crop chemical formulation analysis; foodstuff analysis; biotechnology assays, for example, bacterial and viral particle surface analysis; wear analysis of moving parts, for example, fragmented or wear particulates and the analysis of surface compositions of the fragment particles, such as the presence and extent of liquid or solid sub-particle lubricant or contaminant surface coatings.

Other applications of the system and method of the present invention include, for example, analysis of dosage forms and dosage components, such as dissolution rates after a time, with a measured energy input in aqueous based solvents, that may contain human or animal components like digestive fluids or blood that can be the solvent or liquid phase. The amount of energy expended for dissolution can be correlated to rates of dissolution for different animal or human patients or populations. The sonication or ultrasonication step of the present invention features a highly reproducible and quantifiable energy input that can provide an exacting correlation between dissolution rates and patient profiles. The fertilizer industry can use the present process and invention to further an understanding of fertilization mechanisms, such as absorption rates or binding strengths of various fertilizer components in soil samples, for example, from various depths, and which components can be exposed to various environmental conditions for various periods of time. Efficient and proper mixing of inks and paints can be studied using solid-liquid samples, for example a suspension of pigment particles, or liquid-liquid samples, for example a dispersion of liquid droplet particles in a continuous liquid medium, such as by extraction methods. For workers in the ink and paint industry it is important to know how to make the stable ink and paint suspensions or dispersions so that such products remain stable, that is resistant against separation, precipitation, coagulation, and the like phenomena, for prolonged time periods at various temperatures and humidities. To optimize product stability, one needs to know which component(s) and how much of each component is dissolved or suspended and what energy is needed to achieve a given level of stable dissolution, dispersion, or suspension. The system, apparatus, and methods of the present invention can accomplish this quickly and on a large number of samples in an automated and robotic process.

SUMMARY OF THE INVENTION

Embodiments of the present invention, include:
A method comprising:
  sonicating a liquid suspension of first particles; and
  analyzing the liquid phase for second particles;
An apparatus comprising:
  a sonicator adapted to sonicate a liquid suspension of first particles; and
  a first analyzer adapted to analyze the sonicated liquid phase for second particles.

These and other embodiments of the present invention are illustrated herein.

DETAILED DESCRIPTION OF THE INVENTION

Figure 1:
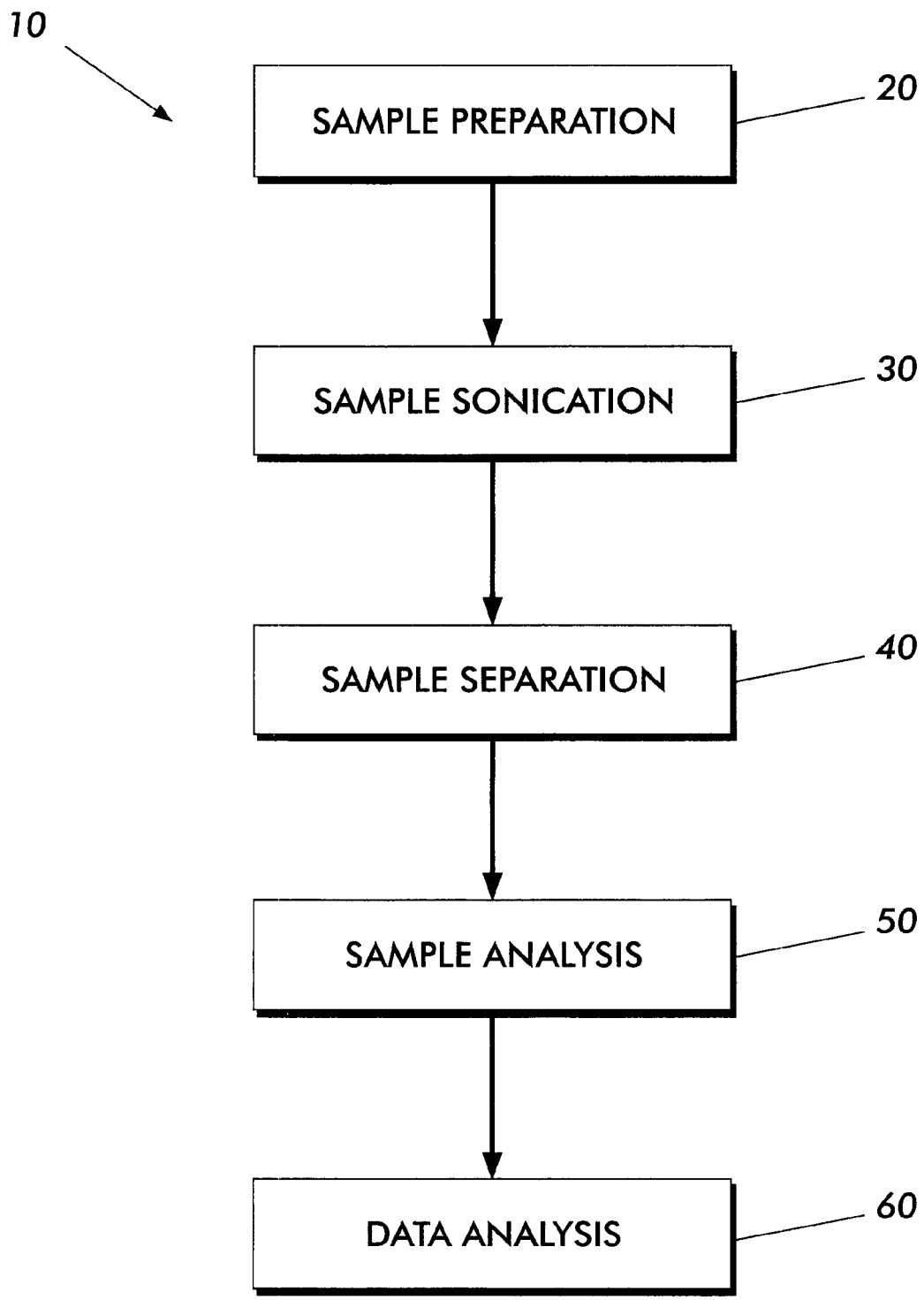
FIG. 1 is a flow chart which illustrates the main stages applied in the system, apparatus, and method, in embodiments of the present invention.

In embodiments the present invention provides a method comprising:
  sonicating a liquid suspension of first particles; and
  analyzing the liquid phase for second particles.

A particularly advantageous and useful feature of the present invention is the capability to measure and determine by calculation, the energy expended in the sonication and to measure and calculate the yield of second particles in the liquid phase. The energy expenditure and the second particle or subsequent particle yield can be correlated to give a measure of the adhesive force between the first particles and the second particles in a natural, ordinary, or nascent state, that is, prior to sonication treatment and associated processing of the present invention.

In embodiments, the sonication can be accomplished, for example, with at least one ultrasonic member. The at least one ultrasonic member or plurality of ultrasonic members can be controlled by any suitable ultrasonic power source, and preferably a high powered ultrasonic source, such as a high powered ultrasonic welding source.

The use of a high powered welding source and controller enables the system to provide an analytical method to provide exact and highly reproducible measure and correlation of the ultrasonic energy required to accomplish a given or measured level of particle suspension, dispersion, or host particle—guest particle separation, and thereby permits a highly reliable and accurate technique for analyzing host particulate-surface particulate compositions. The at least one ultrasonic member can be, for example, in embodiments from one to about ten ultrasonic horns, and preferably from about three to about eight, and most preferably from about four to about six ultrasonic horns. The at least one ultrasonic member can be powered by, for example, a high power ultrasonic welding source, commercially available from Branson, Danbury, Connecticut, which provides exact and reproducible quantities of ultrasonic energy to the ultrasound probe horns, which horns in turn deliver measured doses of ultrasonic energy to the first particle suspension or dispersion. The ultrasonic member or members function to firstly, separate guest or sub-particles, such as toner surface additives, charge control or flow control additives, and the like materials, from the surface of the host or first particles, such as toner particles, and secondly, to suspend the separated sub-particles in the liquid phase. Because of the small size and the surface characteristics of the sub, particles, the sub-particle suspensions, that is the sonicated liquid phase containing the suspended sub-particles, is typically quite stable for considerable periods of time, for example, from about one minute to about one year, and thereby permits convenient manipulation, such as separation from host particles, and analysis thereof as exemplified and illustrated in embodiments of the present invention. Ultrasonic componentry is generally commercially available, for example, from Sonics & Materials, Inc., Newtown, Conn. In the present invention an electrically pulsed energy input is used to produce, for example, up and down movement of an exemplary four horn ultrasonic array. This feature enables, for example, exact control of ultrasonic energy output or delivery to the sample compared to less controllable non-pulsed electrical input used in an alternative ultrasonic array. The diameter and geometry of the ultrasonic horn tip is preferably carefully chosen along with the sample tube configuration, such as a centrifuge tube, to optimize energy dispersion and the ultrasonic separation and surface particle stripping process. The toner sample size and aqueous surfactant solution, for example, to wet hydrophobic toner particles, can be chosen to optimize surface additive particle separation and particulate suspension stability. Additional arrays of, for example, four ultrasonic horns and controller power sources can be used, for example, in a rail station arrangement as an alternative to a circular or carousel station arrangement wherein one or more robots could access and address the rail.

Robotic componentry and robotic system packages can be adapted to, for example, accomplish the robotic automatic sample handling and transfers. Such components and packages are commercially available, for example, from Zymark Corporation, Hopkinton, Mass. Zymark also provides several commercially available robotic modular hands that enable the robot to carry out its intended task. Zymark also makes robotic equipment, for example, see Allegro robots at <http://www.zymark.com/> for extensive uses in the pharmaceutical industry.

In embodiments the process of the present invention can preferably further include separating the first particles from the liquid phase in the resulting sonicated mixture. Although not wanting to be limited by theory the basis for this separation preference resides in a belief that the analysis is easier and more accurate. However, with advances in modem analytical instrumentation the separation step may for certain target analytes or for certain system configurations, the need for a separation or separations of particulates from the liquid phase may be obviated and unnecessary. The separation of the first particles from the liquid phase in the resulting sonicated mixture can be conveniently accomplished by known separation methodologies, for example, centrifugation, filtration, countercurrent distribution, such as fluid flow fractionation, or combinations thereof, and the like known liquid or solid particle-liquid phase and particle-particle phase separation methodologies.

The process of the present invention, in embodiments, can further comprise analyzing the liquid phase for dissolved or suspended analytes which are solubilized or dispersed into the liquid phase from the surface of the first particles during the sonication procedure. The liquid can be, for example, an aqueous liquid, a non-aqueous liquid, a supercritical fluid, a miscible mixture of liquids, an immiscible mixture of liquids, and mixtures thereof, and like combinations. In embodiments, the second particles are preferably liberated from the surface of the first particles during sonication. The method of the present invention can further comprise analyzing the liquid phase for third particles and wherein the third particles can in certain instances be liberated from the surface of the first particles or the second particles during sonication. In embodiments, the third particles preferably are smaller than the second particles and the second particles have smaller third particles on the surface of the second particles. The second particles are known in many industries and technology areas as performance additives, and alternatively or additionally known as, for example, surface additives. Surface additives, for example, in the xerographic imaging technology area can include charge control additives which regulate the charging properties of the toner or developers used in the xerographic process. Similarly, surface additives can include flow additives which generally improve the flow and often the cleaning or removal or other properties of the toner or developer particles.

In embodiments of the process of the present invention, the suspension of first particles can further comprise the inclusion of at least one surfactant in the suspension prior to sonication of the mixture. The surfactant can have any known hydrophobelipophobe balance (HLB) which is effective in achieving the objectives of the present invention, for example, in suspending or dispersing host-guest particle compositions, and for facilitating the analysis of post sonication separated guest particle suspensions or dispersion. A suitable surfactant HLB can be over a broad known range, for example, of from about zero to about eighteen units, preferably with an HLB of from about two to about fifteen units, and most preferably an HLB of from about tree to about fourteen units. It is readily appreciated and understood that the selection of the surfactant and its concomitant HLB will turn, for example, on the nature of the host-guest particle combination, on the relationship of the particle combination upon the matrices used to formulate a host-guest particle suspension, and upon the analytical result or results desired by the operator-analyst. The surfactant can be used in any suitable amount, for example: as used in various particle formulations as in commercial products or experimental formulations; to achieve a stable host-guest particle suspension at the outset of the analysis to facilitate handling and analysis; or to achieve a stable post-sonication separated guest particle suspension or dispersion. Suitable surfactant amounts can be, for example in analyzing toner surface additives, from about 1 to about 10 weight percent and preferably from about 2 to about 5 weight percent based on the weight of the suspended toner particles. It is readily apparent to one of ordinary skill in the art that the surfactant or emulsifier level or concentration can vary over a wide range, for example, from very low concentrations of about several parts-per-million or less to very highly concentrated surfactant formulations of about 70 to 99 weight percent based on the total weight of the formulation. Suitable surfactant materials are known surfactants and dispersants and can include those described in McCutcheon's *Vol. 1: Emulsifiers and Detergents*, North American Ed., McCutcheon Division, MC Publishing Co., 1995, and its predecessor publications, and which publications are incorporated herein by reference in their entirety. In a typical illustrative example, the surfactant, such as an ethoxylate type Triton X-100, commercially available from Rohm & Haas, can be selected at a concentration of from about 0.1 to about 1.0 weight percent based on the weight of the suspension. It is readily understood and appreciated that the surfactant is an optional ingredient in formulating the host-guest particle suspension or dispersion and need not be included when a suitably stable suspension or dispersion can be obtained by other known means, such as by mixed solvent or co-solvent systems, mechanical mixing, such as microfluidization, and the like methods for forming sufficiently stable but temporary mixtures. When a co-solvent is selected it is understood that a co-solvent or mixture of co-solvents can be selected, but, guest-host particle swelling is preferably avoided so as not to unnecessarily confound the analysis. In other embodiments, intentional selection of co-solvents which cause particle swelling can be selected to provide an alternative tool for host-guest particle analysis, for example, to purposely induce particle swelling to demonstrate the extent of guest particle entrapment within the surface of the swollen host particle. Alternatively, the co-solvent can be selected to selectively cause guest particles to swell either while on the surface of the host particle or subsequent to liberation by sonication.

The first particles can be present in the suspension, for example, in an amount of from about 0.1 to about 20 weight percent, preferably from about 1 to about 10 weight percent, and more preferably from about 2 to about 5 weight percent based on the total weight of the suspension. Other first particle weight percentages can be selected depending upon the analytical information desired and the other objectives of the analysis of the present invention. In embodiments, the first particles as host-guest particles can be comprised of, for example, a host toner particle composition with at least one guest particle type as the surface additive. The first particles can also be comprised of a host-guest developer composition comprised of guest toner composition and host carrier particles. Alternatively, in an embodiment, the first particles can be comprised of carrier particles and the second particles can be the toner particles, and the third particles can be the surface additives on the surface of the toner particles. In embodiments, the first particles can be, for example, obtained from a liquid immersion developer composition, for example, either with or without the liquid carrier present. In embodiments the first particles can be a pharmaceutical dosage form. Examples of pharmaceutical dosage forms include but are not limited to known solids, liquids, gels, foams, emulsions, microemulsions, suspensions, such as tablets, crushed tablets, powders, capsules, and the like formulations, which can be suspended, dispersed, or appropriately dissolved in a liquid medium.

As used herein "particle" refers to any discrete unit of material structure including those known entities with size ranges within the size domains of molecular, colloidal, microscopic, or macroscopic measurement. Particles of the present invention, whether the host, guest, or other particles, can include separable solid, liquid, or gaseous entities, and related or alternative entities, and mixtures thereof, such as finely divided solid, liquid, or gas particulates, powders, droplets, bubbles, and the like material dispositions. The present invention in embodiments can be applied to the analysis of host-guest particle combinations or associations including but not limited to, for example, solid-solid, solid-liquid, liquid-solid, liquid-liquid, solid-gas, gas-solid, liquid-gas, gas-liquid, and the like material dispositions. Alternative entities can include for example, foams, gels, slurries, emulsions, microemulsion, miniemulsions, molecular aggregates, high molecular weight molecular solutions and dispersions, and the like known material associations which can retain at least some identifiable, characterizable, distinguishable, or traceable material attribute when subjected to one or more processing step or steps of the present invention.

In an embodiment of the present invention, there is provided a method comprising:

ultrasonicating an aqueous suspension comprised of at least one surfactant and surface treated toner particles;

separating the toner particles from the aqueous phase in the resulting mixture; and measuring the liquid phase for dissolved or suspended surface treatment material stripped from the surface of the surface treated toner particles.

The surface treatment materials can include, for example, but are not limited to known fumed silica materials, with or without a surface treatment or additive on the fumed silica. A particularly preferred fumed silica is one which has been hydrophobically surface treated and wherein the surface treatment is accomplished by physical methods, such as solution coating, or by chemical methods, such as vapor phase reaction with silicon halide compounds followed by hydrolysis.

In still other embodiments of the present invention, there is provided a particle surface analytical method comprising:

sonicating an liquid suspension comprised of host particles surface treated with guest particles;

separating the host particles from the liquid phase in the resulting mixture; and measuring the liquid phase for suspended guest particles stripped from the surface of the surface host particles.

As with the foregoing embodiments, the sonicating can be accomplished with, for example, ultrasound and the like energy dispersive equipment. The liquid suspension of particles can include, for example, at least one surfactant, and which surfactant can aid in the pre-sonication suspension and dispersion of the host particles, post-sonication suspension and dispersion of the liberated guest particles, post-sonication separation of the host particles and liberated guest particles from each other, and post-sonication stabilization of liberated guest particle suspensions. The latter renders the suspended guest particles resistant to agglomeration or deposition from suspension onto, for example, sonicator horns or accumulation of the guest particles as deposits on the walls or bottom of a sample vial. In embodiments, a measure of the liquid phase for suspended guest particles, for example, those stripped from the surface of the host particles by sonication, can be conveniently accomplished with ion coupled plasma (ICP). Historically ICP has been conducted on solutions or solubilized analytes wherein difficult to solubilize materials can be dissolved with strongly corrosive or caustic reagents, and which reagents are expensive to handle and to dispose of and present significant safety concerns and challenges. The present method in embodiments enables suspensions or dispersion of guest or fine particle materials to be readily analyzed by ICP and related analytical methodologies and without the need to solubilize the guest particle material. It is also readily appreciated by one of ordinary skill in the art that the present invention can include an analysis of the separated first particle component, for example by ICP or liquid chromatography-mass spectrum analysis. The analysis of the separated first particle component can be, identical, similar, or unrelated, to the second particle analysis. Where the analysis method selected for the separated components is identical, such as various compositional methods, a before separation and an after-separation measurements can provide a useful "difference" measurement and which measurement can provide an important mass balance accounting and an indicator of any mechanical loss or losses that may inhere to a particular analysis or experimental design configuration.

In embodiments, the method of the present invention can further include correlating the measured amount of suspended or dispersed guest particles in the liquid phase with the surface blending procedures used to prepare the host-guest particles. In embodiments, the method of the present invention can further include thereafter formulating host-guest particles with superior performance properties based upon the correlation information.

In an embodiment of the present invention, there is provided an apparatus comprising:

a sonicator adapted to sonicate a liquid suspension of first particles; and a first analyzer adapted to analyze the sonicated liquid phase for second particles.

The foregoing apparatus can further comprise a number of additional work stations or sites which stations or sites, alone or in combination or conjunction with the other stations, can perform useful functions and can contribute to the overall utility and versatility of the apparatus to, for example, surface particulate adhesion force measurement and diagnosis. Examples of additional work stations include one or more of:

a weigh station, for example, adapted to obtain tare weights, analyte weights, reagent or other additive weights, and the like weights of a typical sample;

a sample preparation station, for example, adapted to suspend or otherwise manipulate the material sample that includes first particles in a liquid or equivalent medium to obtain a liquid or equivalent medium suspension or dispersion of first particles in the liquid, such as a vortexer, vibratory mixer, blender, or the like devices; and a sample separation station adapted to separate the first particles from the liquid or equivalent medium in the resulting sonicated mixture, and wherein the sample separation station can be, for example, one or more of the above mentioned or known separation devices, such as a centrifuge, and the like apparatus.

The apparatus can further comprise a coordinated programmable robot adapted to automate sample preparation and handling tasks, for example, to sequentially advance samples from a sample weigh station, to a sample preparation station, to a sonication station, and for example, advance samples of a prepared liquid suspension of particles from the sonicator to a separation station, and then to a first analyzer station.

The apparatus of the present invention can be used to analyze samples obtained from the sonication step in various states, for example, the first analyzer can analyze the liquid phase in the absence of the first particles, or alternatively or additionally, the first analyzer can analyze the samples or the liquid phase in the presence of the first particles. The inclusion or exclusion of the first particles during the analysis can depend upon, for example, whether the analytical method can distinguish or discriminate, or alternatively ignore, the first particles from any liberated second or third particle analytes of interest.

The apparatus can further comprise a data analysis station adapted to analyze the data from the first analyzer. The data analysis station can be, for example, any suitable computer or equivalent recording device and preferably with a programmable memory, and for example a communications port to permit communication and coordination with other components and devices within the systems or subsequent add-on features. Alternatively or additionally, the data analysis station can communicate and coordinate with other components or devices outside of the systems, for example by wire or by remote or wireless connections. Alternatively or additionally, the data analysis station can be adapted to analyze the data from a second analyzer and where the second analyzer provides additional useful sample information, such as temperature, viscosity, turbidy, particle size, particle number, molecular weight, and the like physical or chemical information. The data analysis station preferably is adapted to correlate the energy expended by the sonicator with the yield of second particles in the sonicated liquid phase to determine the adhesive force between the first particles and is the second particles prior to sonication. In embodiments the first analyzer can be, for example, an ion coupled plasma (ICP) spectrometer, a particle size analyzer, a liquid chromatograph, a gas chromatograph, an ultraviolet-visible spectrophotometer, a mass spectrometer, and the like analyses and instruments, and combinations thereof. Other methods of particle characterization and analysis include for example X-Ray Diffraction (XRD), Atomic Absorption (AA), and methods of electron microscopy, such as Scanning Electron Microscopy (SEM), Transmission Electron Microscopy (TEM) and Analytical Electron Microscopy (AEM). For example, the first analyzer can be adapted to detect the presence of second particles; to measure the particles size properties of the second particles; to measure the conductivity properties of the second particles; and the like analyses. The second analyzer can be, for example one or more of the above mentioned analytical instruments or methods. The second analyzer can alternatively be adapted, for example, to analyze the resulting first particles subsequent to separation from the liquid phase and any liberated second particles.

The sonicator can be, for example, at least one ultrasonic member and a high powered ultrasonic welding source controller, and the at least one ultrasonic member can be, for example, from three to about ten ultrasonic horns. In embodiments, the second analyzer can, for example, analyze the liquid phase for dissolved analytes solubilized from the surface of the first particles by the sonicator. It is readily apparent to one of ordinary skill in the art from a complete understanding of the invention that the second particles can be liberated from the surface of the first particles during sonication. As a control experiment, for example, toner and the like related first particles which were free of second particle surface treatments were sonicated for various intervals of time and intensities of ultrasound with the result that the untreated particles liberated little or no second particles. Thus, it is apparent that untreated first particles do not substantially decompose or degrade under the sonication or subsequent separation or analysis conditions of the present invention and therefore do not confound the analysis of second particles obtained by stripping the second particles from the surface of the first particles which have been previously surface treated. The apparatus of the present invention can be further adapted, for example, to analyze the liquid phase for third particles and wherein the third particles are liberated from the surface of the first is particles, the second particles, or both the first particles and second particles during sonication.

In an exemplary embodiment of the present invention, there is provided an apparatus comprising:

a sample preparation station adapted to generate first particle dispersions, for example, by combining a minor measured amounts of a first particle sample as the disperse phase and major measured amounts of a liquid or equivalent medium as the continuous phase;

an ultrasonication station comprised of a plurality of ultrasonic horns adapted to sonicate first particles dispersions;

a sample separation station adapted to separate first particles from the liquid or equivalent suspending or dispersing medium in the resulting sonicated dispersion;

a sample analysis station adapted to analyze the resulting separated liquid or equivalent medium for any liberated second particles;

a data analysis station adapted to analyze the resulting liberated second particles data from the sample analysis station; and a programmable robot adapted to continuously advance a sample container, for example, with an auto sampler and the like devices, from a blank or empty sample container or tube storage, to the sample preparation station, to the ultrasonication station, to the sample separation station, to the sample analysis station, to the data analysis station, and optionally to a sample retention or discard station.

Figure 3:
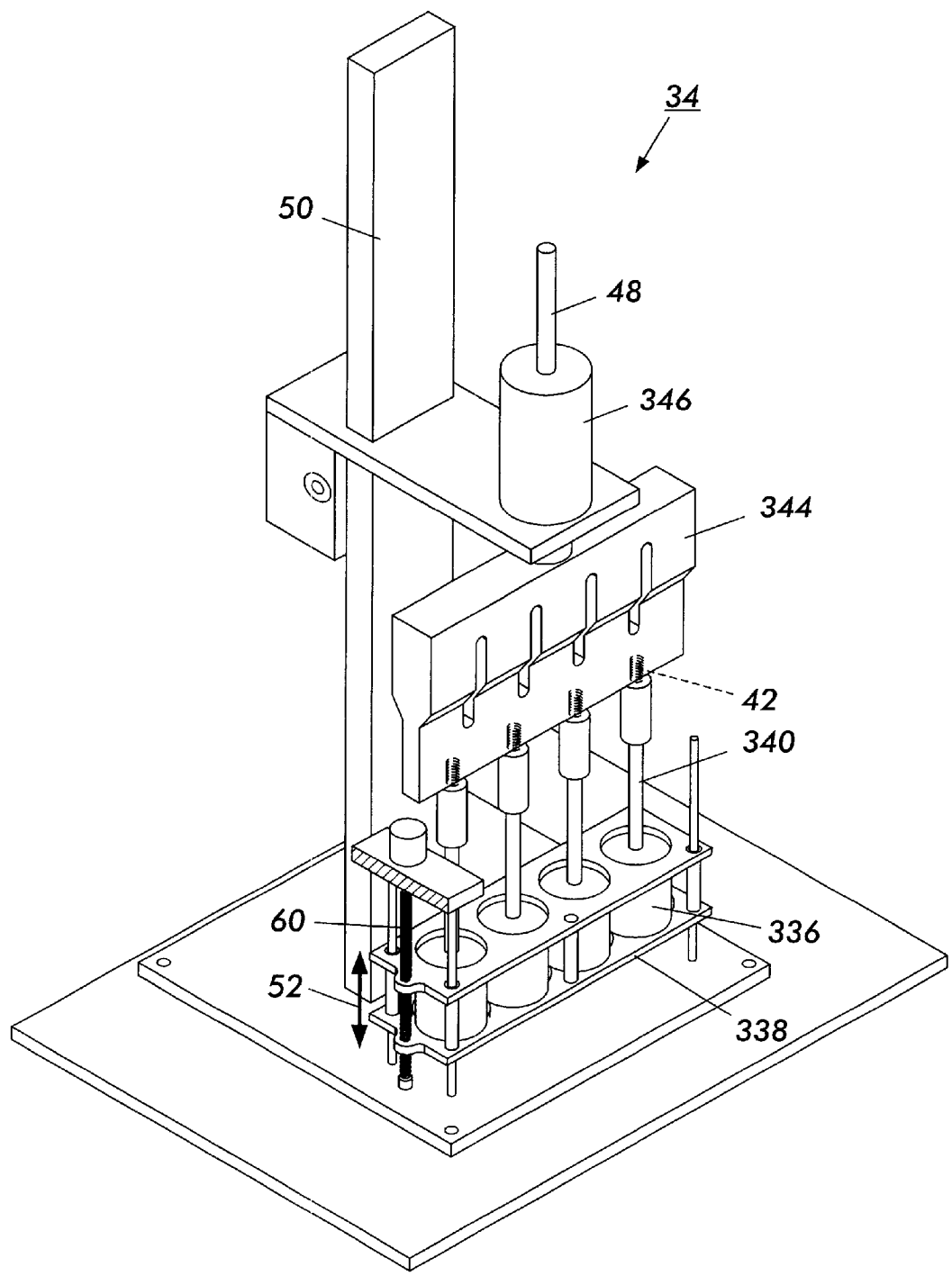
FIG. 3 shows an exemplary configuration of the sonicating members in the sonication station of FIG. 2, in embodiments of the present invention.

It is readily appreciated by one of ordinary skill in the art that the present invention can be embodied in a single sonicating station or apparatus. Thus, for example, a stand-alone sonicating station, for example, as shown in FIG. 3, can include one or more sonicating horns in combination with a suitable power source capable of delivering and recording measured amounts and the duration of the energy delivered and dissipated into a sample or samples. The sample holders, as discussed in further detail below, can be manually or robotically loaded with one or more sample containers, tubes, or vials, and the samples can be irradiated with known and discrete quantities of ultrasonic energy to effect the separation or stripping of guest-host particle combinations into component particle constituents. Additionally or alternatively, a single sonicating station embodiment can include a partial or complete enclosure which can partially or fully isolate the sonication station to further enhance the performance and utility of the present invention. "Isolation" of the sonication chamber refers to and can include, for example: acoustic isolation, that is to reduce or eliminate any noise or audible interference generated by the ultrasound or associated mechanicals or sample processing; environmental isolation, that is, to reduce or eliminate any stray or extraneous emissions for the station or samples under analysis, such as vapors, plumes, spills, and the like effluents from the sonication station. Alternatively or additionally, the environmental isolation can include isolating the chamber and the samples under analysis from external contamination or adjacent sample contamination or cross-contamination. The above mentioned isolation and abatement can be accomplished in embodiments, for example, by enclosing the sonication station in a chamber of PLEXIGLAS® or similar material enclosures, and which chamber or chambers can include for example, one or more sound absorbent or abating materials. Additionally or alternatively, the chamber can include or be situated in a known fume hood or fume removal system which system can be adapted to abate potentially noxious or toxic effluents arising from the samples or sample processing, and optionally to continuously clear the head-space or areas near the samples from potential extraneous contaminants. Additionally or alternatively, the chamber can include known insulation materials which materials adapt the sonicating station to maintaining a desired temperature regime. Additionally or alternatively, the chamber can include known heating or cooling elements adapted to maintain or manipulate the temperature and operating conditions within the sonication chamber and sonication station, for example, analogically or digitally programmably with a thermostat and associated switch and relay connections. Heating or cooling elements can include, for example, know air conditioners for conditioning the atmosphere, such as the temperature and optionally the humidity within the chamber. Alternatively, the sample tubes or the sample holder block can be heated or cooled as desired to maintain, regulate, or otherwise manipulate the temperature of the samples within the chamber.

The present invention in embodiments provides an apparatus comprising:

a sonicator adapted to sonicate at least one liquid suspension of first particles with pulsed ultrasonic energy.

In view of the forgoing discussion it is readily appreciated that the sonicator can have a power source adapted to precisely convert electrical energy to mechanical energy and thereafter divide and deliver the mechanical energy in equal amounts or measure to two or more horn members and consequently to the an appropriately situated sample. The present invention can further comprise an enclosure situated about the sonicator, to form for example, a chamber, and which enclosure is adapted to provide internal and external isolation of the apparatus, samples and sample processing from the surrounding environment. The enclosure contains effluents and prevents their escape into the surrounding environment. Similarly, the enclosure blocks external or environmental influents and prevents their intrusion into the enclosed sonicating chamber and precludes sample contamination and confounding of the analytical results.

The term "station" as used herein broadly and generally refers to, for example, any sample handling or information processing, or loci or module, contained or embodied within the apparatus and method of the present invention.

Referring to the Figures, FIG. 1 shows a flow chart that illustrates, in embodiments, some main stages applied in an exemplary system, apparatus, and method, of the present invention. The system and apparatus can embody, a sequence (10) including but not limited to: sample preparation (20); sample sonication (30); sample separation (40), for example separating solid particles or a precipitate resulting from centrifugation from the liquid or supernatant phase; sample analysis (50), for example wherein the supernatant is analyzed for material arising from the surface of the first particles or original particulate sample with, for example, known methods and instrumentation, such as ICP, liquid chromatography, gas chromatography, and the like analytical methods; and data analysis (60) wherein for example, the data obtained from the sample analysis (50) is, for example, recorded and analyzed for particular target analytes, such as sub-particles or liquid adsorbates which were stripped or liberated from the surface of the first particles. The data analysis can include, for example, both qualitative and quantitative information concerning the surface analytes.

Figure 2:
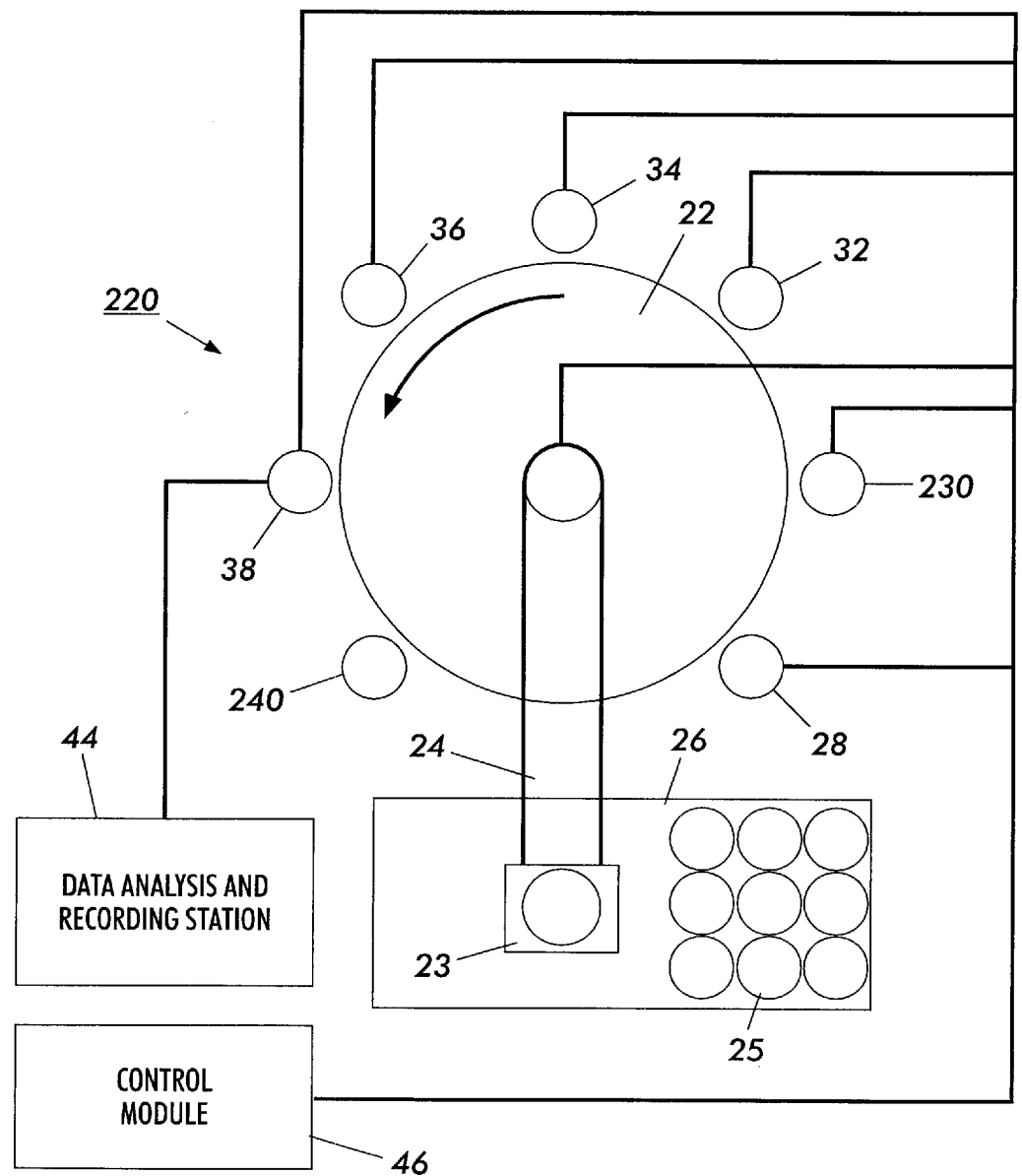
FIG. 2 is an exemplary schematic of a representative system, apparatus, and method, in embodiments of the present invention

FIG. 2 is an exemplary schematic of a representative particle analysis system, apparatus, and method, in embodiments of the present invention, and includes, for example, an automated sample preparation analysis-diagnostic system (220), which can include a robot sample handling system (22), a robot "hand" tool (23) attached to a robot autosampler arm (24) adapted to progammably select from sample tube holder (26)and advance individual sample tubes (25) to the various stations in the system, such as a toner weigh station (28), a weigh station (230) for taring, surfactant and liquid phase addition, a sample mixing station (32) including for example a vibratory or vortex mixer apparatus, a sonication station (34) which can include, for example, the workstation shown in FIG. 3, a centrifugation station (36), a supernatant analysis station (38) which can include one or more of the aforementioned analytical or diagnostic instruments, such as an ICP, an optional sample or tube collection or regeneration station (240), and a data recording and analysis station (44) adapted to record and analyze the data obtained from the supernatant analysis station (38), including for example, a programmable computer with a memory capable of receiving, storing, processing, generating, and displaying results from operating on the input data. The aforementioned system components are preferably connected and fully integrated with a system control module (46) which can ensure seamless interaction of components and continuous operation of the system and can include a communications linkage to and between individual system components and optionally includes an external communications linkage, for example, to a network which connections can provide, for example, system status, results, and alert information to a remote operator. In embodiments the robotic hand tool can be configured to hold a centrifuge tube, and can be adapted to hold virtually any comparably sized tube, jar, bottle, and the like containers by, for example, including an inner liner of VITON® elastomer (not shown) which material is found for example, in fuser roll applications. The VITON® liner provides a superior container grip and also provides a non-stick surface which avoids contaminant attachment or fouling.

FIG. 3 shows an exemplary configuration of the sonicating members in the sonication station of FIG. 2. More specifically, FIG. 3 shows a multi-probe ultrasonic workstation (34) of the present invention including, for example, an optional PLEXIGLAS® or the like dust proof enclosure (not shown), a sample block (336) for receiving and securely retaining from a preceding station, by way of robotic or manual transfer, one or more sample vials or tubes (338). The samples in tubes (338) are individually and respectively acted upon by ultrasonic horn members (340). Multiple horn members (340) can be attached by any suitable means, such as a precision machined and countersunk screw or tapping (42) to multiplexed horn member (344) which member (344) is known and commercially available and which horn member (344) is known to be useful by itself, for example, to accomplish ultrasonic press welding of sheet materials. The horn member (344) is connected to power source converter (346) which converts electrical source energy (48) to ultrasonic mechanical energy which is transferred to the horn members (340) and thereafter dissipated into the samples contained in tubes (338) to effect the stripping of surface constituents from host particles. The foregoing componentry can be conveniently supported and properly aligned, for example, on stand (50) or an equivalent structure. The sample block (336), in embodiments, can be proximally delivered to horn members (340) by an elevator or similar lift means, such as a worm gear (60), which lift provides precision vertical displacement (52) of the sample block to enable either ultrasonication of samples when elevated or robot or manual access and sample interchange when depressed. The lift means or elevator is preferably attached to a servo-motor (not shown) and which motor is preferably electronically linked to the system control module (46) of FIG. 2 to coordinate the placement sample block for appropriate operations and to optionally preclude the operation of the ultrasonic horns (40) in the absence of, for example, a complete set of sample tubes (25).

An exemplary embodiment of the particle analytical system, apparatus, and method of the present invention follows. Robotics can be employed to move samples to and from the various processing stations or analysis stations in the system. As an initial step, a robot can be used to tare a sample or centrifuge tube and cap combination at a weigh station. Next, the robot removes the cap from the tarred sample vial and a powdered target sample, such as a toner or any other suitable solid, is placed into the tube. The cap is placed back atop the sample tube and the tube is reweighed and the amount of powder by difference from the tare is computed and recorded. At the next station, the cap is removed and a prescribed quantity of surfactant solution is added to the tube and then recapped. At the next station, a constant vortex mixing for a prescribed time wets the toner. At the next station, the cap is removed and the tube is placed along with three other tubes beneath the four ultrasonic horns. The horns when energized can move up and down in regular pulses, to systematically and controllably effect the separation of the surface additive from the solid particle, such as a surface additive treated toner formulation.

The ultrasonic horn tips can be constructed of, for example, titanium or other suitably hard metal or metals to avoid damage from hard or abrasive solids for example, toner additives, such as magnetites and titanias. Alternatively, the horns can be coated with a suitable protective coating, such as a inert polymer, diamond film, or other equivalent and suitably inert material, to further protect the horns from, for example, corrosion or material deposition, and the like potential changes in the sample or the horn members. After the ultrasonication step, the tube is recapped and then delivered to the centrifuge station, where centrifugation is accomplished. After centrifugation, the tube is transported to the final station at which the cap is removed and the liquid phase is aspirated from the sample vial or tube into the analytical instrument or instruments of choice for analysis of the liquid phase material. For toner applications, the analytical tool is, for example, an Inductively Coupled Plasma (ICP) unit. Generally, ICP analysis results obtained from suspensions are not very reproducible. However, because the particle suspensions formed in the present invention ultrasonic step are so complete and stable, ICP analysis results from the inventive ultrasonic step can be duplicated many times over and with high precision and accuracy. Other analytical instruments can be used in addition to, or in place of, an ICP to carry out other analyses. For example, in a non-toner application, a centrifuged supernatant or liquid phase could be robotically injected into a liquid chromatography (HPLC) or gas chromatography (GC) unit to separate, identify, and quantify the soluble or insoluble components contained in the liquid phase.

Figure 4:
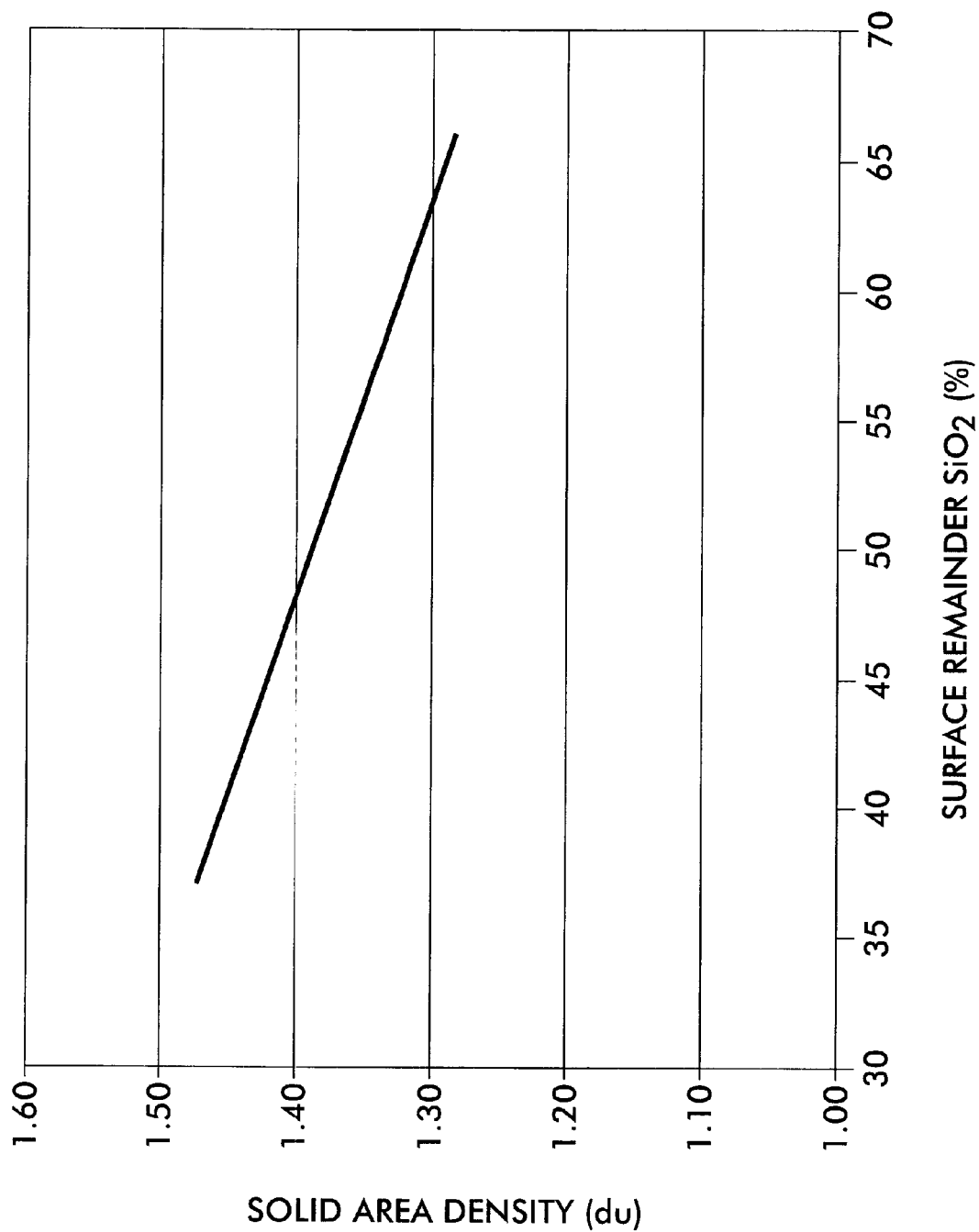
FIG. 4 shows the relation between the adhesion force measurements obtained with the present invention and solid area density measurements obtained from images prepared from toner formulations with surface additives with various levels of surface treatment and adhesion.

Referring to FIG. 4 the graph shows an exemplary relation between adhesion force measurements, in terms of surface remainder silicon dioxide, that is guest particle $SiO_2$ remaining on the surface of host toner particles, as obtained with the present invention and solid area density (SAD) measurements obtained with images prepared from toner formulations with surface additives at various levels of surface treatment and adhesion. The data as plotted and fitted with the line shown in the Figure provides a high level of correlation of, for example, solid area density (SAD) as measured with a densitometer from solid area printed images and expressed in density units with the residual $SiO_2$ remaining on the surface of various sonicated $SiO_2$ surface treated toner samples.

Other advantages of the present invention include but are not limited to, for example, reduced sample analysis time, for example by a factor of from about 1.5 to about 10 fold; reduced sample size, for example, by from about 1.5 to about 10 fold compared to conventional ultrasonic sample sizes; providing a excellent screening tool for product development and product formulation, for example, situating and understanding the influence of surface additive constituents or contaminants; and the like advantages. Other advantages of the present invention include, for example: improved spatial design involving the linear array of ultrasonic horns and a robotic hand design which can universally grip various sizes and shapes of sample-centrifuge tubes; ultrasonic horns constructed of titanium or related metals, alloys, or include protective coating to improve wear of the ultrasonic horn tip; and a software data analysis and feedback mechanism to provide real-time adjustments in the parameters used for the host-guest particle separation and analysis.

The invention will further be illustrated in the following non limiting Examples, it being understood that these Examples are intended to be illustrative only and that the invention is not intended to be limited to the materials, conditions, process parameters, and the like, recited herein. Parts and percentages are by weight unless otherwise indicated.

COMPARATIVE EXAMPLE I

In a preliminary but unsuccessful system design two ultrasonic horns were combined with one or more non-pulsed power supplies. These non-pulsed power supply configurations failed when additional horns were serially incorporated, for example, due to a rapid decay in horn energy output. This failure mode made the analysis results non-reproducible and highly unreliable. Other attempts to deliver consistent levels of ultrasonic energy to liquid suspensions, dispersion, emulsions, and the like formulations failed because the alternative configurations used a circular arrangement of horns at the ultrasonic station making robot arm access difficult. More importantly, they failed because the electrical power (watts) delivered by the non-pulsed electrical power sources did not translate into equal amounts of ultrasonic energy (joules) output from the four horns.

EXAMPLE I

SAMPLE PREPARATION

A 0.5 gram sample of surface treated toner was weighed into a centrifuge tube. To the tube was added 15 mL of Triton-X100 surfactant, commercially available from Rohm & Haas, and deionized water to afford a surfactant in water at about 0.4 weight percent. The mixture was suspended with a vortex mixer for set period of about ten to about sixty seconds and then sonicated for a set period of time and a set or predetermined, that is programmed, amount of sonic energy.

SONICATION

A commercially available Branson plastic welding power source was selected and it was coupled to four commercially available ultrasonic horns to obtain a system capable of providing precise energy output from each horn for an unlimited number of ultrasonic events and samples. The welding power source delivers energetic pulses to the ultrasonic horns and enables a precise, repeatable, and measurable energy output from each horn to each sample container. Thus, electrical power was reproducibly converted to mechanical power in the vibrating ultrasonic horn. About a one second burst of electrical power or energy, as measured for example in Watts or Joules, for example, about 500 Joules, from the pulsed power source enabled the four ultrasonic horns to reproducibly vibrate the horn tips up and down for thirty seconds, that is, to provide mechanical energy as measured in joules to the sample. The pulsed time interval can be readily adjusted or varied. In embodiments the energy dispersed into the sample can be, for example, from about 1.0 to about 40 kilojoules, with the amount depending upon the desired result and other factors inherent to the method of the present invention discussed above.

SAMPLE WORK-UP AND ANALYSIS

The resulting sonicated mixture was centrifuged, for example, for two minutes at 1,000 revolutions per minute. The supernatant was separated and was analyzed by, for example, inductively coupled plasma (ICP) spectroscopy to quantitate the level of silica as measured by Si parts per million in the sample. The present analytical method, in robotic embodiments provides an overall estimated precision and reproducibility of five percent RSD compared to completely manual embodiments which provide an overall estimated precision and reproducibility of ten percent RSD.

Other modifications of the present invention may occur to one of ordinary skill in the art based upon a review of the present application and these modifications, including equivalents thereof, are intended to be included within the scope of the present invention.

What is claimed is:

1. A method comprising:
   sonicating a liquid suspension of first particles;
   analyzing the liquid phase for second particles; and
   further analyzing the liquid phase for dissolved analytes solubilized from the surface of the first particles during the sonication.

2. The method in accordance with claim 1, wherein the energy expended in the sonication and the yield of second particles in the liquid phase is correlated to the adhesive force between the first particles and the second particles prior to sonication.

3. The method in accordance with claim 1, wherein the sonication is accomplished with at least one ultrasonic member.

4. The method in accordance with claim 3, wherein the at least one ultrasonic member is controlled by a high powered ultrasonic welding source.

5. The method in accordance with claim 3, wherein the at least one ultrasonic member is from one to about ten ultrasonic horns.

6. The method in accordance with claim 1, further comprising separating the first particles from the liquid phase in the resulting sonicated mixture.

7. The method in accordance with claim 1, wherein separating the first particles from the liquid phase in the resulting sonicated mixture is accomplished by centrifugation, filtration, countercurrent distribution, or combinations thereof.

8. The method in accordance with claim 1, wherein the liquid is an aqueous liquid, a non-aqueous liquid, or miscible and immiscible mixtures thereof.

9. The method in accordance with claim 1, wherein the second particles are liberated from the surface of the first particles during sonication.

10. The method in accordance with claim 1, further comprising analyzing the liquid phase for third particles wherein the third particles are liberated from the surface of the first particles or the second particles during sonication.

11. The method in accordance with claim 1, wherein the first particles have smaller second particles on the surface of the first particles.

12. The method in accordance with claim 1, wherein the suspension of first particles further comprises at least one surfactant.

13. The method in accordance with claim 12, wherein the surfactant has an HLB of from about zero to about eighteen units.

14. The method in accordance with claim 1, wherein the first particles are present in the suspension in an amount of from about 0.1 to about 20 weight percent based on the total weight of the suspension.

15. The method in accordance with claim 1, wherein the first particles are comprised of a toner composition with at least one surface additive.

16. The method in accordance with claim 1, wherein the first particles are comprised of a developer composition comprised of toner composition and carrier particles.

17. The method in accordance with claim 1, wherein the first particles are from a liquid immersion developer composition.

18. The method in accordance with claim 1, wherein the first particles are a pharmaceutical dosage form.

19. A method comprising:
ultrasonicating an aqueous suspension comprised of at least one surfactant and surface treated toner particles;
separating the toner particles from the aqueous phase in the resulting mixture; and
measuring the liquid phase for dissolved or suspended surface treatment material stripped from the surface of the surface treated toner particles.

20. The method in accordance with claim 19, wherein the surface treatment material is a fumed silica.

21. The method in accordance with claim 20, wherein the fumed silica is hydrophobically surface treated.

22. A method comprising:
ultrasonicating a liquid suspension of host-guest particles comprised of host particles surface treated with guest particles;
separating the host particles from the liquid phase in the resulting mixture; and
measuring the liquid phase for suspended guest particles stripped from the surface of the surface host particles.

23. The method in accordance with claim 22, wherein the liquid suspension further comprises at least one surfactant.

24. The method in accordance with claim 22, wherein measuring the liquid phase for suspended guest particles stripped from the surface of the surface host particles is accomplished with ion coupled plasma (ICP).

25. The method in accordance with claim 22, further comprising correlating the measured amount of suspended guest particles in the liquid phase with the surface blending procedures used to prepare the host-guest particles.

26. The method in accordance with claim 25, further comprising formulating host-guest particles with superior performance properties based upon the correlation.

27. A method according to claim 22, wherein said host particles comprise a toner.

* * * * *